US008882729B2

(12) United States Patent
Horstmann et al.

(10) Patent No.: US 8,882,729 B2
(45) Date of Patent: Nov. 11, 2014

(54) TRANSDERMAL THERAPEUTIC SYSTEM HAVING STABILIZED MEMBRANE

(75) Inventors: Michael Horstmann, Neuwied (DE); Patrick Mohr, Breisig (DE); Mohammad Sameti, Bonn (DE)

(73) Assignee: LTS Lohmann Therapie Systeme AG, Andernach (DE)

( * ) Notice: Subject to any disclaimer, the term of this patent is extended or adjusted under 35 U.S.C. 154(b) by 779 days.

(21) Appl. No.: 12/921,988

(22) PCT Filed: Feb. 28, 2009

(86) PCT No.: PCT/EP2009/001446
§ 371 (c)(1),
(2), (4) Date: Dec. 15, 2011

(87) PCT Pub. No.: WO2009/112167
PCT Pub. Date: Sep. 17, 2009

(65) Prior Publication Data
US 2012/0245537 A1    Sep. 27, 2012

(30) Foreign Application Priority Data

Mar. 11, 2008 (DE) .......................... 10 2008 013 701

(51) Int. Cl.
*A61M 35/00* (2006.01)
*A61K 9/00* (2006.01)
*A61K 9/70* (2006.01)
(52) U.S. Cl.
CPC ............. *A61K 9/7084* (2013.01); *A61K 9/0014* (2013.01)
USPC ................ 604/289; 424/449; 602/48; 602/54
(58) Field of Classification Search
USPC ............................ 604/289, 290; 424/443, 449
See application file for complete search history.

(56) References Cited

U.S. PATENT DOCUMENTS

| 4,781,924 | A | 11/1988 | Lee et al. |
| 5,215,751 | A | 6/1993 | Muller et al. |
| 6,221,383 | B1 * | 4/2001 | Miranda et al. ............... 424/449 |
| 6,620,429 | B1 | 9/2003 | Muller et al. |
| 6,884,434 | B1 | 4/2005 | Muller et al. |
| 7,175,853 | B1 | 2/2007 | Bracht |
| 2004/0253299 | A1 | 12/2004 | Beier et al. |
| 2005/0169977 | A1 * | 8/2005 | Kanios et al. ................. 424/449 |

FOREIGN PATENT DOCUMENTS

| DE | 39 05 050 | 8/1990 |
| DE | 39 05 051 | 8/1990 |
| DE | 198 14 083 | 10/1999 |
| DE | 198 14 084 | 10/1999 |
| DE | 198 14 087 | 10/1999 |
| EP | 0 316 065 | 5/1989 |
| WO | WO 93/10772 | 6/1993 |
| WO | WO/96/39136 | 12/1996 |
| WO | WO 97/11696 | 4/1997 |
| WO | WO 03/011291 | 2/2003 |

OTHER PUBLICATIONS

International Search Repot dated Jun. 17, 2009, 4 pgs.

* cited by examiner

*Primary Examiner* — Melanie Hand
(74) *Attorney, Agent, or Firm* — Frommer Lawrence & Haug LLP

(57) ABSTRACT

The invention relates to a transdermal therapeutic system made of the following layers: a carrier layer (T), an active ingredient layer (R), a membrane layer (M) and optionally an adhesive layer (K), wherein the carrier layer (T) is impenetrable to the active substance and to water, the active substance layer (R) comprises as an active substance component the salt of an alkali reactive active substance, such as a CNS-active amine in combination with at least one alkali reactive further component, and a polymer component (P1), wherein the active substance is released from the active substance layer (R) only by the moisture entering from the exterior through the membrane layer (M), and the membrane layer (M) is made of a polymer component (P2), allowing a uniform delivery of basic active substances to the skin.

17 Claims, No Drawings

TRANSDERMAL THERAPEUTIC SYSTEM HAVING STABILIZED MEMBRANE

The present invention relates to transdermal therapeutic systems and their production. Transdermal therapeutic systems (TTS) are forms of pharmaceutical administration which can be applied to the skin of a mammal and are designed to make a drug, following transdermal uptake, available systemically. Transdermal therapeutic systems can increase the therapeutic value of the administration of a drug by ensuring a constant delivery of the active ingredient into the blood compartment over a prolonged time period. The advantages of this continuous delivery of active ingredient are primarily the extended intervals of application, which result in improved patient compliance, and the pharmacokinetically improved time profile of the plasma concentration, which ensures a longer time of action with fewer side effects. Other advantages arising from the transdermal administration route by means of a transdermal therapeutic system are reduced dosage, improved gastrointestinal compatibility, and increased bioavailability as a result of circumvention of what is called the first pass effect.

On the basis of these advantages, transdermal therapeutic systems have for some few years been enjoying increasing popularity in the therapy of diverse diseases. Transdermal systems of this kind have been introduced into therapy for—for example—the active ingredients estradiol, nicotine, norethisterone acetate, fentanyl, tulobuterol, ethynylestradiol, buprenorphine, and nitroglycerine. The structure of a transdermal therapeutic system is generally thin and laminar, and so, with the aid of the layer directly facing the skin, an at least temporarily adhesive bond to the skin is produced, via which the active ingredient is delivered. TTS consists typically of a backing layer (T) which is impervious to the drug, an active ingredient-containing layer (R), such as an active ingredient layer or matrix layer, for example, and an adhesive layer (K) for attachment to the skin.

This adhesive layer (K) may also be identical with the drug or active ingredient layer (e.g., active ingredient layer or matrix layer). The TTS further usually comprises a protective layer which is drug-impervious and is intended for removal prior to application, called the release liner. To enhance delivery of active ingredient there may also be a membrane layer (M) provided, which controls delivery to the skin.

Permeation of the particular active ingredient from the TTS through the skin is improved using not only various solid polymers (e.g., polyacrylates, silicones, polyisobutylenes), resins, and other pharmaceutical excipients, but also various system components which are liquid at room temperature, and which in some cases allow adjustment of the bond strength and of the improvement in diffusion within the transdermal therapeutic system, or else serve to improve the permeation of active ingredient through the skin.

Not only the active ingredients used but also the excipients used, which are often liquid, may have properties which are disruptive to the production of TTS, such as volatility and/or thermal instability under the operating conditions, for example. This may have the consequence that, in the course of the process of producing the transdermal systems, which frequently consists of the mixing of the starting materials in a suitable organic solvent, their subsequent coating in a thin layer on a base sheet, and drying, usually continuous drying, at an elevated temperature thereafter, considerable losses occur.

These losses, particularly of expensive active ingredients, not least during the final production stage of the TTS, the drying, may result in missed dosages and/or performance reductions in the TTS produced. These technical problems may limit, or rule out the possibility of, proper production and an appropriate therapeutic application, particularly in humans.

Transdermal therapeutic systems in different embodiments (e.g., reservoir with and without membrane) have been in use for many years for different active ingredients and therapies. For reasons of improved control of the supply of active ingredient, many transdermal systems are characterized spatially by a suitable compartmentalization, into—for example—an active ingredient layer (R), a membrane layer (M), and an adhesive layer (K). Also known are transdermal systems which, for reasons of the stability of the active ingredient, comprise the active ingredient initially in the form of a salt, and make it available only after reaction with, for example, alkaline substances.

A technical drawback effecting these systems, however, is that their release is frequently uncontrolled and/or they necessitate an addition of liquid alkaline reagents that is technically difficult to implement.

The transdermal therapeutic systems of the prior art in the field of alkaline active ingredients have a range of further drawbacks. For instance, a frequent drawback of membrane/reservoir systems which contain the alkaline active ingredient already in solution is that the dissolved active ingredient initially present, via the connection of the membrane, and owing to the diffusion, enriches the adhesive layer (K) with high concentrations of active ingredient. This high concentration in the adhesive layer (K) is reduced only after several hours of wear to a level which is given by the theoretical apportionment of the permeation rate on the basis of the membrane permeation.

The unwanted, initially high uptake of active ingredient via the skin may, first, lead to increased skin reactions. Furthermore, the incidence of relatively high blood level peaks of active ingredient at the beginning of the wear of the TTS is likely to have corresponding side effects. Another drawback of these known systems is the frequently poor stability of alkaline active ingredients in a membrane preparation. Numerous oxidation, ester cleavage, and hydrolysis reactions may alter the active ingredient in the course of long-term storage. In contrast, the majority of alkaline active ingredients in salt form are extraordinarily stable.

It is an object of the present invention to provide a transdermal therapeutic system (TTS) which is suitable for a stability-sensitive, volatile and/or skin-irritating active ingredient (W), this active ingredient (W) being brought into a form which allows membrane-controlled supply of active ingredient. Furthermore, the TTS is to have a shelf life of at least two years without significant formation of degradation products of the active ingredient. The TTS is also to exhibit good or at least satisfactory compatibility on human or animal skin.

These technical objects are achieved by means of a transdermal therapeutic system (TTS) comprising, and preferably consisting substantially of, the following layers:
  a) a backing layer (T),
  b) an active ingredient layer (R),
  c) a membrane layer (M), and optionally
  d) an adhesive layer (K),
the backing layer (T) being impervious to the active ingredient and preferably to water as well, the active ingredient layer (R) comprising as active component (WK) the salt of an alkaline active ingredient (W) in combination with at least one alkaline further constituent (B) and also a polymeric component (P1), the active ingredient (W) being released from the active ingredient layer (R) only as a result of the moisture from the active component (WK), which migrates in from the outside through the membrane layer (M) (for example, from the skin of the patient), and the membrane layer (M) being composed of a polymeric component (P2).

As far as the various polymeric components of the different layers of the TTS are concerned, there are numerous possibilities for selection.

In one preferred embodiment of the transdermal therapeutic systems of the invention, the active ingredient layer is constructed as a matrix system.

This is a system in which the adhesive or nonadhesive polymer matrix comprises the active component, generally in dissolved and/or suspended form. Often in this case the polymer matrix is composed of pressure-sensitive adhesives based on polyacrylates. The polyacrylates used in that case are prepared from monomers (acrylic acid and methacrylic acid and also their respective esters, optionally also with vinyl acetate), which may contain functional groups. These functional groups are able to withstand the polymerization of the monomers employed, while remaining unchanged, and are able to influence the properties of the resultant polyacrylate, particularly the tack and the adhesiveness.

EP-A 0 614 356 discloses examples of polyacrylate-based adhesive formulations of this kind. The skilled person distinguishes between polyacrylates with —OH groups (hydroxyl groups) and those with —COOH groups (carboxyl groups) as functional groups. The hydroxyl-containing polyacrylates include, for example, the commercial product DuroTak 87-2287. The carboxyl-containing polyacrylates include, for example, the product DuroTak 87-2051. Both polyacrylates are provided by the manufacturer, National Starch (Bridgewater, USA).

These polyacrylates have proven to be stable and highly compatible adhesive polymers for the production of matrices for the transdermal therapeutic systems.

A disadvantage effecting the transdermal therapeutic systems comprising polyacrylates which contain the stated functional groups (hydroxyl group, carboxyl group) is the poor active ingredient utilization rate. This is observed particularly with hormonal transdermal therapeutic systems. A poor active ingredient utilization rate in this context means that, after the expiry of the envisioned application time of the transdermal therapeutic system, a relatively large amount of the active ingredient, in comparison to the total amount of active ingredient present in this transdermal therapeutic system prior to commencement of administration, remains unutilized in the transdermal therapeutic system.

Since active ingredients that are in some cases expensive are used in the transdermal therapeutic systems of the invention, the poor active ingredient utilization rate is undesirable from both economic and environmental standpoints. Finally, in the case of active pharmaceutical ingredients which are toxic at relatively high concentration, a high residual content may also constitute a potential hazard for improper intake of a higher dose.

In accordance with the invention, this disadvantage is resolved by means of a transdermal therapeutic system in which the active ingredient layer (R) stabilizes the active ingredient such that, in the unused TTS, it does not cross to any substantial extent into the membrane layer. As active component (WK) for this purpose it is possible to use the salt (e.g., a hydrochloride) of an alkaline active pharmaceutical or other ingredient (W) in combination with an alkaline further constituent (B), such as disodium hydrogen phosphate, calcium oxide, sodium phosphate or sodium caprylate, for example. Silicates too have proven a possible component.

In this way it is ensured that the transdermal therapeutic system is activated only after the removal of the protective layer (S) and after having being adhered to the skin, by means of the moisture (perspiration) of the skin that migrates into the TTS. The moisture that migrates into the active ingredient layer (R) through the membrane layer (M) releases the base of the active ingredient (W) in the active ingredient layer (R), and so, via the membrane layer (M), the active ingredient (W) can be delivered continuously to the skin of—for example—the patient.

In addition to the diffusiveness of the membrane layer (M) for moisture and active ingredient (W), a significant stability is achieved relative to systems without a membrane layer. As a result it is possible, for the adhesive layer (K), to use even polymeric components (P3) which without this layer display a significant tendency toward cohesive fracture.

The invention further provides a transdermal therapeutic system in which the active ingredient layer (R) comprises an inorganic salt of an alkaline active ingredient (W) and an inorganic, alkaline constituent (B) and also as polymeric component (P1) a polyacrylate, polysilicone, polyisobutylene (PIB) or a styrene (block) copolymer (SBS, SIS, SBR), for example. The invention also relates to a transdermal therapeutic system where the membrane layer (M) is composed of a moisture-permeable polymeric component (P2).

The invention further provides a transdermal therapeutic system wherein the active ingredient layer (R) in addition to 1% to 50% (m/m) of at least one salt of an active pharmaceutical ingredient also comprises 1% to 20% (m/m) of at least one alkaline further constituent (B) and also 30% to 90% (m/m) of at least one polymeric component (P1).

The invention also relates to a transdermal therapeutic system where the active ingredient layer (R) is a polymer matrix which in addition to 5% to 40% (m/m) of at least one salt of an active pharmaceutical ingredient also comprises 5% to 20% (m/m) of at least one alkaline further constituent (B) and also 40% to 80% (m/m) of at least one polymeric component (P1).

The invention further provides a transdermal therapeutic system wherein the active ingredient layer (R) is a polymer matrix based on a polyacrylate or on a silicone polymer and comprising not only 5% to 40% (m/m) of at least one salt of an active ingredient having at least one amino function but also 5% to 20% (m/m) of an alkaline inorganic constituent (B).

The invention also relates to a transdermal therapeutic system where the active ingredient layer (R) is a polymer matrix based on a polyacrylate or on a silicone polymer which as active component (WP) comprises an inorganic salt of an active ingredient for the treatment of disorders of the central nervous system (CNS), in combination with an alkaline inorganic constituent (B), the weight ratio between the salt of the active ingredient and the constituent (B) being from 1:10 to 10:1, preferably 1:7 to 7:1.

The invention also provides a transdermal therapeutic system where the active ingredient layer (R) is a polymer matrix based on a polyacrylate which is substantially free of functional groups.

The invention also relates to a transdermal therapeutic system which as well as a polymeric membrane layer (M) has an additional adhesive layer (K) which is composed of a polymeric component (P3), such as a polyacrylate or a silicone polymer, for example.

The invention also relates to a method of producing a transdermal therapeutic system, where applied to a backing layer (T), comprising, for example, a polymer or aluminum foil, at least one active ingredient layer (R) which comprises as active component (WK) the salt of an alkaline active ingredient (W) in combination with at least one alkaline further constituent (B) and also a polymeric component (P1), subsequently a membrane layer (M) comprising a polymeric component (P2), made of polyvinyl acetate, for example, is applied, and optionally an adhesive layer (K) comprising a polymeric component (P3), comprising, for example, a self-adhesive polyacrylate, and also, optionally, further layers (e.g., a protective layer) are added.

Additionally, the use of a salt of an alkaline active ingredient (W) in combination with at least one alkaline further constituent (B) and a polymer for producing a pharmaceutical formulation, more particularly a TTS, for treating diseases in humans and animals is provided by this invention.

In the context of the use, it is also possible to employ an inorganic salt of an alkaline active ingredient (W) in combination with at least one alkaline further constituent (B) and a polyacrylate for producing a transdermal therapeutic system for treating CNS diseases in humans.

As polymeric component (P1) for the active ingredient layer (R) it is possible, for example, to use a polyacrylate (or else a silicone polymer), e.g., a polyacrylate containing a reduced fraction of hydroxyl groups and/or carboxyl groups. As polymeric component (P1) it is also possible to use a polyacrylate which is substantially free of functional groups.

Polyacrylates contemplated for possible use in the active ingredient layer, which may be substantially free of functional groups, include, for example, homopolymers, copolymers, and block copolymers based on acrylic esters and/or methacrylic esters. Contemplated particularly in this context as monomers for preparing the polyacrylate are n-butyl acrylate, n-butyl methacrylate, ethyl acrylate, 2-ethylhexyl acrylate, ethyl methacrylate, methyl acrylate, methyl methacrylate, tert-butyl acrylate, sec-butyl acrylate, tert-butyl methacrylate, cyclohexyl methacrylate, 2-ethylhexyl methacrylate, isobornyl methacrylate, isobutyl methacrylate, isopropyl acrylate, isopropyl methacrylate, and mixtures of these monomers.

The monomers are frequently esters of acrylic and/or methacrylic acid which carry linear, branched or cyclic aliphatic $C_1$-$C_{12}$ substituents without other functional groups. It is also possible to use vinyl acetate as a comonomer together with at least one of these monomers for preparing the polyacrylate.

By the esters of acrylic acid and/or methacrylic acid which carry functional groups and are suitable for producing the active ingredient layer, and which may be present in the monomer mixture used for preparing the polyacrylate, are meant, primarily, esters containing hydroxyl groups, i.e., 2-hydroxyethyl acrylate, 2-hydroxyethyl methacrylate, 3-hydroxypropyl acrylate, and 3-hydroxypropyl methacrylate. Compounds such as acrylonitrile, methacrylonitrile, acrylamide, dimethylaminoethyl acrylate may also be regarded in the context of this description as esters of acrylic and/or methacrylic acid with functional groups. The fraction of the sum of acrylic acid, methacrylic acid, 2-hydroxyethyl acrylate, 2-hydroxyethyl methacrylate, 3-hydroxypropyl acrylate and/or 3-hydroxypropyl methacrylate in the monomer mixture used for preparing the polyacrylate should not be too large.

By "substantially free of functional groups" is meant, in the sense of the present description, that the total fraction of acrylic acid, methacrylic acid, and esters of acrylic acid and methacrylic acid that carry functional groups is below 2% by weight in the polyacrylate.

The monomer mixtures for producing the active ingredient layer may be polymerized in a variety of ways, as for example ionically, free-radically, under light induction, in which case, if desired, crosslinkers are used, such as aluminum acetylacetonate, allyl glycidyl ether and/or glycidyl methacrylate, for example. If desired, preparation also takes place with use of auxiliaries such as antioxidants, stabilizers, and/or alkyl mercaptans. Emulsifiers or organic solvents may also be used as a reaction medium.

Preferred polymeric components (P1) are, for example, the acrylic acid polymer GMS 3083 from the manufacturer Cytec, or the silicone polymers BioPSA from the manufacturer Dow Corning.

Polymeric components (P2) preferred for producing the membrane layer (M) are, for example, polymers of the polyolefin type (e.g., polyvinyl acetate (PUA) or polypropylene (PP)), polyurethanes, and silicones.

Polymeric components (P3) that are preferred for producing the adhesive layer (K) for application to the membrane layer (M) are, for example, the following polymers: polyacrylates such as, for example, DuroTak 87-2287; silicone polymers (such as, for example, PSA 7-4202) or polyisobutylenes.

Particularly suitable as an alkaline constituent (B) which is used together with the salt of the active ingredient in the active ingredient layer (R) are the following substances: CaO, $Na_2HPO_4$, silicates, $Na_3PO_4$, Na caprylate.

In one particularly simple embodiment the active ingredient layer (more particularly the polymer matrix) is composed exclusively of the active ingredient salt, an alkaline constituent (B), and the polymer (P1), preferably a polyacrylate. Also possible are embodiments in which a mixture of a polyacrylate without functional groups with a polyacrylate with functional groups is used.

As well as the preferred active ingredients for the therapy of central nervous system diseases (such as memantine and ropinirole), a very wide variety of active pharmaceutical ingredients, alone or in combination, may be used as active components.

Contemplated for this purpose, for example, are the following active ingredients, with the basic active ingredients and/or salts thereof being of more particular interest:

alpha-adrenoceptor agonists such as, for example, xylometazoline, adrenolone, clonidine, ephedrine, tiamenidine, β-adrenoceptor agonists such as, for example, formoterol, terbuterol, ritodrine, alpha-adrenoceptor blockers such as, for example, dapiperazole, doxazosin, prazosin, yohimbine, trimazosin β-adrenoceptor blockers such as, for example, acebutolol, atenolol, bisoprolol, bopindolol, bupranolol, propanolol, metoprolol, nadolol, pindolol, timolol, anabolics such as, for example, androstenediol, bolandiol, clostebol, 4-hydroxy-19-nortestosterone, methenolone, narcotics such as, for example, alfentanil, buprenorphine, codeine, dimenoxadol, fentanyl, isomethadone, lofentanil, methadone, morphine, morphine derivatives, normethadone, normorphine, propiram, sufentanil, tilidine, analgesics (non-narcotics) such as, for example, aminopyrine, antipyrine, aspirin, benoxaprofen, bucetin, clometacin, keterolac, androgens such as, for example, boldenone, fluoxymesterone, mestanolone, mesterolone, methandrostenolone, 17-methyltestosterone, 17α-methyl-testosterone-3-cyclopentyl enol ether, norethandrolone, normethandrone, oxandrolone, oxymetholone, prasterone, stanolone, stanozolol, testosterone, testosterone 17-chloral hemiacetal, testosterone 17β-cypionate, testosterone enanthate, testosterone nicotinate, testosterone phenylacetate, testosterone propionate, tiomesterone, anesthetics such as, for example, amucaine, amylocalne, biphenamine, cocaine, diperodon, ecgonidine, euprocin, fenalcomine, fomocaine, hexylcaine, hydroxydione, hydroxyprocaine, hydroxytetracaine, ketamine, leucinocaine mesylate, levoxadrol, lidocaine, mepivacaine, meprylcaine, metabutoxycaine, methohexital, midazolam, naepaine, octacaine, orthocaine, oxethazaine, parethoxycaine, phenacaine, piperocaine, polidocanol, pramoxine, prilocalne, procaine, propanocaine, propofol, risocaine, tetracaine, thialbarbital, thiamylal, thiobutabarbital, thiopental, tolycaine, trimecaine, zolamine, antiallergics such as, for example, amlexanox, astemizole, azelastine, cromolyn, fenpiprane, histamine, repirinast, tiaramide, tranilast, traxanox, urushiol, ketotifen, nedocromil, oxatomide, pentigetide antiandrogens such as, for example, bifluranol, cyoctol, cyproterone, oxendrolone, antianginals such as, for example, amlodipine, amyl nitrite, cinepazet maleate, imolamine, isosorbide dinitrate, limaprost, molsidomine, nitroxyalkylamide derivatives, antiarrhythmics such as, for example, acecamide, adenosine, ajmaline, alprenolol, amoproxan, aprindine, bretylium tosylate, bubumolol, bunaftine, butidrine, butobendine, meobentine, mexiletine, moricizine, pirmenol, pronethalol, propafenone, pyrinoline, penicillins such as, for example, amdinocillin, pivoxil, amoxicillin, ampicillin, apalcillin, aspoxicillin, azidocillin, azlocillin, bacampicillin, benzylpenicillin, carbenicillin, carfecillin, carindacillin, clometocillin, cloxacillin, cyclacillin, dicloxacillin, diphenicillin, epicillin, fenbenicillin, floxicillin, hetacillin, lenampicillin, metampicillin, methicillin, mezlocillin, nafcillin, oxacillin, penamecillin, penethamate hydriodide, penicillin G benethamine, penicillin G benzathine, penicillin G benzyhydrylamine, penicillin G calcium, penicillin G hydrabamine, penicillin N, penicillin O, penicillin V, penicillin V benzathine, penicillin V hydrabamine, penimepicyclin, phenethicillin, piperacillin, pivapicillin, propicillin, quinacillin, sulbenicillin, talampicillin, temocillin, tiacarcillin, antidiabetics such as, for example, sulfonylurea derivatives, acetohexamide, carbutamide, chlorpropamide, glibornuride, gliclazide, glimepiride, glipizide, gliquidone, glisoxepide, glyburide, glybuthiazole, glybuzole, glyhexamide, glymidine, glypinamide, phenbutamide, tolazamide, tolbutamide, tolcyclamide, acarbose, benzylthiazolidine-2,4-dione, calcium mesoxalate, miglitol, antihistaminics such as, for example, acrivastine, bamipine, brompheniramine, chlorpheniramine, dimethindene, metron S, pheniramine, pyrrobutamine, thenaldine, tolpropamine, triprolidine, bietanautine, bromodiphenhydramine, carbinoxamine, clemastine, diphenylpraline, doxylamine, embramine, medrylamine, mephenhydramine, p-methyldiphenhydramine, orphenadrine, phenyltoloxamine, piprinhydrinate, setastine, alloclamide, chloropyramine, chlorothen, histapyrrodine, methafurylene, methaphenilene, methapyrilene, phenbenzamine, pyrilamine, talastine, thenyldiamine, thonzylamine, tripelennamine, zolamine, cetirizine, chlorcyclizine, clocinizine, hydroxyzine, tricyclics, antimigraine agents, hydrogenated ergot alkaloids, β-adrenoreceptor blockers, antagonists, serotonin antagonists, platelet aggregation inhibitors, antidepressants such as, for example, alpiropride, dihydroergotamine, ergocornine, ercocorninine, ergocryptine, ergot, ergotamine, flumedroxone acetate, fonazine, methysergide, oxetorone, pizotyline, sumatriptan, anagrelide, argatroban, cilostazol, daltroban, defibrotide, enoxaparin, Fraxiparin, indobufen, lamoparan, ozagrel, picotamide, plafibride, tedelparin, ticlopidine, triflusal, bronchodilators such as ephedrine derivatives such as, for example, albuterol, bambuterol, bitolterol, carbuterol, clenbuterol, chlorprenaline, dioxethedrine, eprozinol, etafedrine, ethylnorepinephrine, fenoterol, hexoprenaline, isoetharine, isoproterenol, mabuterol, metaproterenol, N-methylephedrine, pirbuterol, procaterol, protokylol, reproterol, rimiterol, soterenol, terbutaline, tulobuterol, estrogens such as, for example, benzestrol, broparoestrol, chlorotrianisene, dienestrol, diethylstilbestrol, diethylstilbestrol dipropionate, dimestrol, fosfestrol, hexestrol, methallenestril, methestrol, colpormon, equilenin, equilin, conjugated estrogenic hormones, estrogen esters, estropipate, 17β-estradiol, estradiol, estradiol benzoate, estradiol 17β-cypionate, estriol, estrone, ethinylestradiol, mestranol, moxestrol, mytatrienediol, polyestradiol phosphate, quinestradiol, quinestrol, gestagens such as, for example, allylestrenol, anagestone, chlormadinone acetate, delmadinone acetate, demegestone, desogestrel, dimethisterone, dydrogesterone, ethinylestrenol, ethisterone, ethynodiol, ethynodiol diacetate, fluorogestone acetate, gestodene, gestonorone caproate, haloprogesterone, 17-hydroxy-16-methyleneprogesterone, 17α-hydroxyprogesterone, 17α-hydroxygesterone caproate, levonorgestrel, lynestrenol, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, promegestone, quingestrone, trengestone, vasodilators such as, for example, bencyclane, ciclonicate, cinnarizine, citicoline, diisopropylamine dichloroacetate, eburnamonine, fenoxedil, ibudilast, ifenprodil, nafronyl, nicametate, nicergoline, ninodipine, papaverine, pentifylline, tinofedrine, vincamine, vinpocetine, amotriphene, bendazol, benfurodil hemisuccinate, benziodarone, chloracyzine, chromonar, clobenfurol, clonitrate, dilazep, dipyridamole, dropenilamine, efloxate, erythritol, erythrityl tetranitrate, etafenone, floredil, ganglefene, hexestrol bis(β-diethylaminoethyl ether), hexobendine, isosorbide dinitrate, itramin tosylate, khellin, lidoflazine, mannitol hexanitrate, medibazine, nicorandil, nitroglycerine, pentaerythritol tetranitrate, pentrinitrol, pimethylline, prenylamine, propatyl nitrate, pyridofylline, trapidil, tricromyl, trimetazidine, trolnitrate phosphate, visnadine, bamethan, betahistine, bradykinin, brovincamine, bufeniode, buflomedil, butalamine, cetiedil, ciclonicate, cinepazide, cyclandelate, eledoisin, hepronicate, inositol niacinate, isoxsuprine, kallidin, kallikrein, moxisylyte, nicofuranose, nylidrin, piribedil, suloctidil, xanthinal and niacinate, and nicotine.

It is preferred to use basic active CNS ingredients, more particularly amines.

Preference is additionally given to using the following salts of the active ingredients with the following anions: Cl$^-$, PO$_4^{3-}$, HPO$_4^{2-}$, H$_2$PO$_4^-$, acetate, maleate, Br$^-$, I$^-$, oxalate, nitrate, carbonate, HCO$_3^-$, and stearates.

The invention is also illustrated by the examples below.

EXAMPLE 1

A transdermal therapeutic system containing an active antidementia ingredient is produced using the components identified in the table below (figures in % M/M), the active ingredient used being a salt of memantine.

| Components | Amount [%] |
| --- | --- |
| Active ingredient salt: Memantine HCl | 30.0 |
| Constituent (B): CaO | 7.5 |
| Polymer (P1): acrylate polymer GMS 3083 | 62.5 |

EXAMPLE 2

A transdermal therapeutic system containing an active antidementia ingredient is produced using the components identified in the table below (figures in % M/M), the active ingredient used being a salt of memantine (e.g., hydrochloride).

| Components | Amount [%] |
| --- | --- |
| Active ingredient salt: Memantine HCl | 40.0 |
| Polymer (P1): basic "butylated methacrylate copolymer" | 20.0 |
| Excipient: Na caprylate | 10.0 |
| Membrane layer (M): acrylate polymer Durotak 2287 | 30 |

In example 2, the membrane layer (M) functions simultaneously as adhesive layer (K). In addition, however, depending on the active ingredient (W) and constituent (B), it is possible to use a further membrane layer (M), with, for example, polyvinyl acetate (PVA) or polypropylene (PP) as polymeric component (P2). Bonding on the skin side is accomplished via a polyacrylate-based adhesive layer (K).

As a protective layer (S) in both of examples 1 and 2 it is possible to use a polyethylene terephthalate film. The amounts of active ingredient delivered to the skin from each of the active ingredient layers, via the membrane layer, can be measured in a Franz's cell, which is known to the skilled person.

The invention claimed is:

1. A transdermal therapeutic system (TTS) comprising the following layers:
   a backing layer (T);
   an active ingredient layer (R);
   a membrane layer (M); and
   optionally an adhesive layer (K);
   wherein the backing layer (T) is impervious to an alkaline active ingredient (W);
   wherein the active ingredient layer (R) comprises:
      an active component (WK) which is a salt of the alkaline active ingredient (W);
      at least one alkaline further constituent (B); and
      a polymeric component (P1);
   wherein the membrane layer (M) comprises a polymeric component (P2);
   wherein the alkaline active ingredient (W) is released from the active ingredient layer (R) only after moisture migrates in from the outside of the TTS through the membrane layer (M) so as to contact the active component (WK); and
   wherein the active ingredient layer (R) is arranged in between the backing layer (T) and the membrane layer (M).

2. The transdermal therapeutic system of claim 1;
   wherein the active component (WK) is an inorganic salt of the alkaline active ingredient (W);
   wherein the at least one alkaline further constituent (B) is an inorganic alkaline further constituent; and
   wherein the polymeric component (P1) is a polyacrylate or polysilicone.

3. The transdermal therapeutic system of claim 1;
   wherein the polymeric component (P2) of the membrane layer (M) is moisture-permeable.

4. The transdermal therapeutic system of claim 1;
   wherein the active ingredient layer (R) comprises:
      1% to 50% (m/m) of the active component (WK);
      1% to 20% (m/m) of the at least one alkaline further constituent (B); and
      30% to 90% (m/m) of the polymeric component (P1).

5. The transdermal therapeutic system of claim 1;
   wherein, the active ingredient layer (R) comprises:
      5% to 40% (m/m) of the active component (WK);
      5% to 20% (m/m) of the at least one alkaline further constituent (B); and
      40% to 80% (m/m) the polymeric component (P1).

6. The transdermal therapeutic system of claim 1;
   wherein the active ingredient layer (R) is a polymer matrix based on a polyacrylate or on a silicone polymer, and comprises:
      55 to 40% (m/m) of the active component (WK), which has at least one amino function; and
      5 to 20% (m/m) of the at least one alkaline further constituent (B), which is an alkaline responsive inorganic constituent.

7. The transdermal therapeutic system of claim 1;
   wherein the active ingredient layer (R) is a polymer matrix based on a polyacrylate or on a silicone polymer;
   wherein active component (WK) is an inorganic salt of an active CNS ingredient
   wherein the at least one alkaline further constituent (B) is an alkaline inorganic further constituent; and
   wherein the weight ratio between the active component (WK) and the further constituent (B) is from 1:10 to 10:1.

8. The transdermal therapeutic system of claim 1;
   wherein the active ingredient layer (R) is a polymer matrix based on a polyacrylate concerns which is substantially free of functional groups.

9. The transdermal therapeutic system of claim 1, further comprising:
   an additional adhesive layer (K) which is composed of a polymeric component (P3).

10. A method of producing the transdermal therapeutic system of claim 1, comprising:
    applying the active ingredient layer (R) to the backing layer (T);
    subsequently applying the membrane layer (M); and
    optionally adding an adhesive layer (K) comprising a polymeric component (P3).

11. A method of treating a disease in a patient in need thereof, comprising:
    administering a therapeutically effective amount of the alkaline active ingredient (W) via application of the transdermal therapeutic system of claim 1.

12. The method of claim 11;
    wherein the disease is a CNS disease.

13. The method of claim 12;
    wherein the disease is Alzheimer's disease and the active ingredient is memantine.

14. The method of claim 2;
    wherein the active ingredient layer (R) comprises:
       5% to 40% (m/m) of the active component (WK);
       5% to 20% (m/m) of the at least one alkaline further constituent (B); and
       40% to 80% (m/m) the polymeric component (P1);

wherein the active ingredient layer (R) is a polymer matrix based on a polyacrylate or on a silicone polymer;

wherein the active component (WK) is an inorganic salt of an active CNS ingredient; and wherein the weight ratio between the active component (WKS) and the further constituent (B) is from 1:10 to 10:1.

15. The transdermal therapeutic system of claim 14;
wherein the active ingredient layer (R) is a polymer matrix based on a polyacrylate concerns which is substantially free of functional groups.

16. The transdermal therapeutic system of claim 14;
wherein the active ingredient (W) is memantine.

17. The transdermal therapeutic system of claim 15;
wherein the active ingredient (W) is memantine.

* * * * *